United States Patent
Hani et al.

(10) Patent No.: US 9,079,857 B2
(45) Date of Patent: Jul. 14, 2015

(54) PROCESS FOR PREPARING ALKALI METAL PYRITHIONE AND ITS POLYVALENT METAL COMPLEXES FROM PYRIDINE OXIDE

(71) Applicant: Arch Chemicals, Inc., Atlanta, GA (US)

(72) Inventors: Rahim Hani, Alpharetta, GA (US); John J. Jardas, Rochester, NY (US); Richard Dumas, East Haven, CT (US); David Lei, Alpharetta, GA (US)

(73) Assignee: Arch Chemicals, Inc., Atlanta, GA (US)

( * ) Notice: Subject to any disclaimer, the term of this patent is extended or adjusted under 35 U.S.C. 154(b) by 5 days.

(21) Appl. No.: 13/838,470

(22) Filed: Mar. 15, 2013

(65) Prior Publication Data

US 2013/0261309 A1  Oct. 3, 2013

Related U.S. Application Data

(60) Provisional application No. 61/619,485, filed on Apr. 3, 2012.

(51) Int. Cl.
  *C07F 1/04* (2006.01)
  *C07D 213/89* (2006.01)
  *C07D 213/70* (2006.01)

(52) U.S. Cl.
  CPC ............ *C07D 213/70* (2013.01); *C07D 213/89* (2013.01)

(58) Field of Classification Search
  USPC .................................................. 546/2, 347
  See application file for complete search history.

(56) References Cited

U.S. PATENT DOCUMENTS

| | | | |
|---|---|---|---|
| 2,951,844 A | 9/1960 | Shermer | |
| 3,047,579 A | 7/1962 | Witman | |
| 3,159,640 A | 12/1964 | McClure et al. | |
| 3,203,957 A | 8/1965 | Kirchner | |
| 3,297,556 A | 1/1967 | Boudakian | |
| 3,590,035 A | 6/1971 | Damico | |
| 3,700,676 A | 10/1972 | Damico | |
| 3,773,770 A | 11/1973 | Damico | |
| 3,899,495 A | 8/1975 | Beschke et al. | |
| 4,080,329 A | 3/1978 | Muntwyler | |
| 4,396,766 A | 8/1983 | Farmer, Jr. et al. | |
| 4,504,667 A | 3/1985 | Katz et al. | |
| 4,585,871 A | 4/1986 | Boudakian | |
| 5,536,376 A | 7/1996 | Yamaguchi et al. | |
| 5,869,678 A | 2/1999 | Schiessl et al. | |

FOREIGN PATENT DOCUMENTS

| | | |
|---|---|---|
| DE | 2208007 | 9/1973 |
| DE | 2717325 | 11/1977 |
| JP | S 58088362 | 5/1983 |
| JP | S 58152867 | 9/1983 |
| JP | S 59112968 | 6/1984 |
| JP | H 01308255 | 12/1989 |
| KR | 20020031981 | 5/2002 |

OTHER PUBLICATIONS

International Search Report and Written Opinion, PCT/US2013/034882, mailed May 15, 2013.
J. Chinese Medicine Industry, 21(7), 317, 1990.
Jie Song, Guangzhou Huaxue, 28(1), 23-25,58, 2003 (Abstract).
Zheng et.al., Huaxue Shijie (Chemical world), 34(9), 437-40, 1993 (Abstract).
International Preliminary Report on Patentability, mailed Oct. 7, 2014.

*Primary Examiner* — Charanjit Aulakh
(74) *Attorney, Agent, or Firm* — Dority & Manning, P.A.

(57) ABSTRACT

The present invention generally relates to a novel process for preparing alkali metal pyrithione from pyridine N-oxide, using a sulfurination agent and a base agent. In particular, the present invention relates to an efficient process for preparing polyvalent metal complexes of sodium pyrithione from the alkali metal pyridine N-oxide described herein.

22 Claims, No Drawings

PROCESS FOR PREPARING ALKALI METAL PYRITHIONE AND ITS POLYVALENT METAL COMPLEXES FROM PYRIDINE OXIDE

RELATED APPLICATIONS

This application claims priority under 35 U.S.C. §119(e) from U.S. Ser. No. 61/619,485 filed Apr. 3, 2012, entitled "A NOVEL PROCESS FOR PREPARING A ALKALI METAL PYRITHIONE AND ITS POLYVALENT METAL COMPLEXES FROM PYRIDINE OXIDE". The disclosure of U.S. Ser. No. 61/619,485 is incorporated herein by reference in its entirety.

FIELD OF THE INVENTION

This invention generally relates to a process for preparing alkali metal pyrithione from pyridine N-oxide, using a sulfurination agent, and a base agent. In addition, the invention relates to an efficient process for preparing polyvalent metal complexes of pyrithione from the alkali pyrithione described herein.

BACKGROUND OF THE INVENTION

Pyrithione (also known as 2-mercaptopyridine-1-oxide, 2-pyridinethiol-1-oxide, and 2-pyridinethione) and monovalent metal salts (Li, Na and K) and polyvalent metal salts (Mg, Ca, Zn and Cu) of pyrithione are well known antimicrobial agents, and widely used as fungicides, bactericides and preservatives/mildewicide in antidandruff shampoo, antifouling paint, metal working fluid, fish-farming net, architecture paints and other industrial, household and building products.

Sodium pyrithione is an important intermediate for producing polyvalent salts of pyrithione, in particular, zinc pyrithione and copper pyrithione, which are widely used as biocides. It has been a challenging task to produce sodium pyrithione more efficiently and economically to meet the increasing market demand.

Scheme 1 shows a conventional method for preparing sodium pyrithione, which includes the steps of: 1) chlorination of pyridine 1 to 2-chloropyridine 2; 2) oxidation of 2 to 2-chloropyridine N-oxide 3; 3) mercaptization of 3 with sodium hydrosulfide or sodium sulfide to sodium pyrithione 4; and 4) complexation of 4 with a divalent metal salt ($ML_2$ where $L_2=Cl_2$, $SO_4$; M=Mg, Ca, Sr, Ba, Zn and Cu) to produce metal salts of pyrithione 5.

Scheme 1

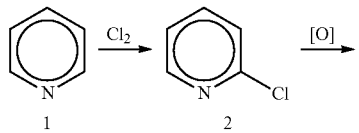

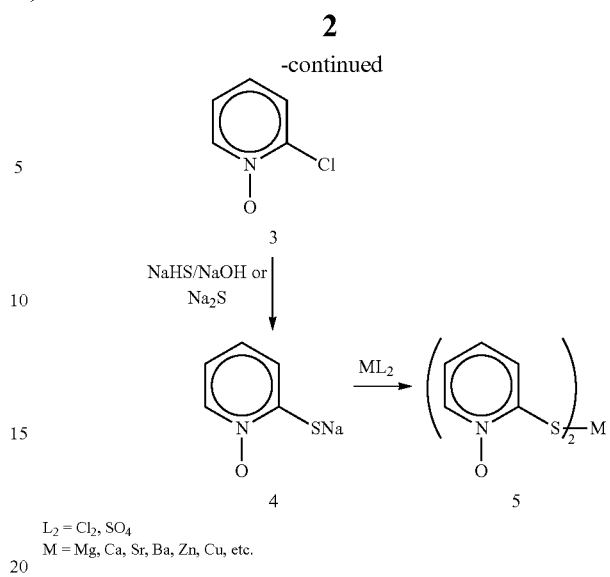

$L_2 = Cl_2$, $SO_4$
M = Mg, Ca, Sr, Ba, Zn, Cu, etc.

In scheme 1, mercaptization of 2-chloropyridine N-oxide 3 can be achieved with either sodium sulfide, or sodium hydrosulfide/sodium hydroxide (DE2717325, U.S. Pat. No. 4,080, 329). Mercaptization of 3 using sodium sulfide or sodium hydroxide is a clean reaction and generates a nearly quantitative yield of sodium salt of pyrithione 4. Further, metal complexation of resulting 4 with polyvalent metal salt of chloride and sulfate produces the corresponding metal pyrithione 5 having high purity and in high yield (U.S. Pat. Nos. 4,396,766 and 3,159,640).

However, the process shown in scheme 1 includes complex chlorination of pyridine 1 and incomplete oxidation of 2-chloropyridine 2 to produce relative low yield of products. Although unreacted 2-chloropyridine 2 can be recovered, the recovery process requires a costly separation of 2-chloropyridine from reaction mixtures containing either unreacted pyridine and other chlorinated pyridines, or 2-chloropyridine N-oxide and catalyst. Therefore, many efforts have been focused on improving the chlorination and oxidation steps of scheme 1.

2-chloropyridine 2 have been prepared by thermal and photochemical chlorination of 1 (DE2208007; U.S. Pat. No. 3,297,556; U.S. Pat. No. 5,536,376; Jpn Kokai Tokkyo Koho, JP 01 308,255, 1989; J. Chinese medicine industry, 21(7), 317, 1990; and Guangzhou Huaxue (2003), 28(1), 23-25, 58). Both thermal and photochemical chlorination processes are complex, and generally result in a product mixture containing the unreacted pyridine 1, the desired 2-chloropyridine 2, and a mixture of 2,6-dichloropyridine, 3-, 4-, 5-chloropyridine and tar. Sequential purification of 2-chloropyridine from the reaction mixtures is an expensive and lengthy process. Oxidation of 2-chloropyridine 2 to 2-chloropyridine N-oxides 3 is more difficult than chlorination of pyridine 1 to 2 because of electron-withdrawing properties of the chlorine. Early attempts that involved the oxidation of 2 with peroxy acids gave a moderate yield of the product, but multiple recycling of the unreacted starting materials was necessary (U.S. Pat. No. 2,951,844). This oxidation was later improved using peracetic acid, which was generated in situ from hydrogen peroxide and acetic acid, in the presence of a catalyst to give 2-chloropyridine N-oxide 3 in a yield ranging from 40-68%. Catalysts used for this purpose included maleic acid, maleic acid anhydride or phthalic acid anhydride (U.S. Pat. No. 4,504, 667), sulfuric acid and sodium hydrosulfate (U.S. Pat. No. 4,585,871), tungstic acid (U.S. Pat. No. 3,047,579), or heterogeneous polymer with sulfonic acid and carboxylic acid moieties (U.S. Pat. No. 5,869,678). U.S. Pat. No. 3,203,957 discloses a process to improve the oxidation of 2, by using 70% hydrogen peroxide, one equivalent of maleic acid anhydride as catalyst, and methylene chloride as a solvent. However, this process does not improve the yield of 3.

The above prior art oxidation methods require complex and costly separation processes, including recovery of large amount of unreacted starting material 2, and disposal or recovery of substantial amount of acetic acid and catalyst. Further, large amount of salts of the acids remaining in the aqueous phase with the 2-chloropyridine N-oxide 3 product causes problems for subsequent reaction steps of Scheme 1.

Another approach for preparing polyvalent metal pyrithione is shown in Scheme 2, which involves three steps starting from pyridine and does not include a chlorination step. Scheme 2 comprises the steps of oxidation of pyridine 1 to pyridine N-oxide 6, sulfurination of 6 with a sulfurinating agent in the presence of a base agent followed by metal complexation of sodium pyrithione 4 with a corresponding polyvalent metal salt to form the corresponding metal pyrithione 5.

Scheme 2

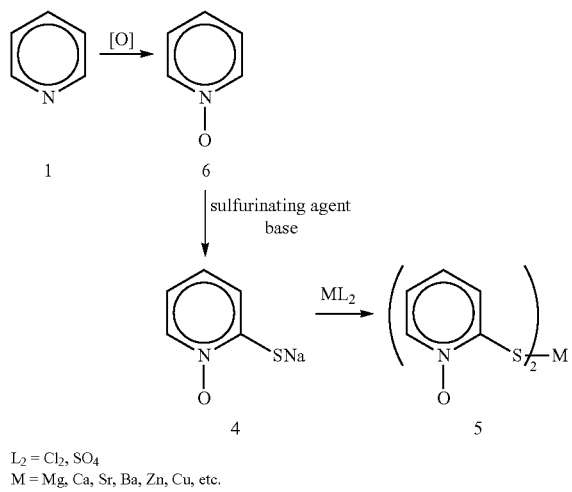

$L_2 = Cl_2, SO_4$
$M = Mg, Ca, Sr, Ba, Zn, Cu, etc.$

Scheme 2 does not involve complex chlorination steps, and it involves a more facile oxidation of pyridine rather than the oxidation of 2-chloropyridine shown in scheme 1. The oxidation of pyridine, as shown in Scheme 2, under similar conditions used for the oxidation of 2-chloropyridine in Scheme 1, results in nearly quantitative yield of pyridine N-oxide 6. Thus, no recovery of pyridine is needed.

One aspect in which the prior art processes differ as to one another is the type of bases used for generating the active carbon anion of pyridine N-oxide 6, which then reacts with a sulfurinating agent to form sodium pyrithione 4. U.S. Pat. Nos. 3,590,035 and 3,700,676 disclose the use of sodium hydride, butyllithium and potassium tert-butoxide for generating the carbon anion of pyridine N-oxide. The resulting carbon anion was treated with elemental sulfur or sulfur chloride to produce sodium or lithium pyrithione, respectively. The bases used in these methods are not cost effective, and the product yield is about 40%. JP 58088362, 59112968 and 58152867 disclose using a weaker base, sodium hydroxide, for generating the carbon anion. According the methods disclosed in JP 58088362, 59112968 and 58152867 pyridine N-oxide 6 was first treated with NaOH to generate the carbon anion of 6 and then reacted with elemental S or SCl in the presence of an organic solvent such as DMF and toluene to form sodium pyrithione having a yield of about 10%, based on the pyridine N-oxide.

Until Zheng et. al. (Huaxue Shijie, 34(9), 437-40, 1993), data on the quality of polyvalent salts of pyrithione made from the direct sulfurination of pyridine N-oxide was unavailable. Zheng et. al. modified scheme 2 and generated sodium pyrithione from reaction of 6 with elemental sulfur and sodium hydroxide in DMSO/toluene. The resulting sodium pyrithione was then converted to zinc pyrithione having brown color and with a yield of about 20% yield. The low yield and the brown color of zinc pyrithione are not acceptable for commercialization applications.

More recently, potassium tert-butoxide was used to generate the carbon anion of pyridine N-oxide 6 in an organic solvent (KR Application No. 10-2000-0062795) and the resulting carbon anion was treated with 30 times of elemental sulfur to produce potassium pyrithione in 65-73% yield. However, potassium pyrithione was not isolated and its quality was not reported. Excess sulfur used in the process is not only expensive, but makes separation of product difficult. More importantly, there is no data of polyvalent metal pyrithione made from this process, and thus the quality, color and purity, of polyvalent metal pyrithiones is unknown.

U.S. Pat. No. 3,773,770 discloses a method for producing sodium pyrithione comprising decarboxylation of 2-picolinic acid N-oxide or its salt to the carbon anion of 6 followed by treatment of 6 with elemental sulfur. Sodium pyrithione generated from this process is converted to polyvalent metal pyrithiones having a low yield of about 40% with unacceptable quality.

Sodium pyrithione and polyvalent pyrithione generated using prior art methods are not cost effective, and do not meet color and purity specifications set for commercial application. For example, zinc pyrithione often requires at least 98% purity with white or off-white color to meet specifications for antidandruff shampoo formulation, and copper pyrithione requires a purity that will not cause gelation of antifouling paint.

Thus, there is a need to overcome the above-stated product quality problems and high cost associated with the processes. In particular, there is a need to provide a better method for producing high yield of sodium pyrithione from pyridine N-oxide that gives high quality of polyvalent metal pyrithione, particularly, zinc pyrithione with white or off white color.

SUMMARY OF THE INVENTION

Accordingly, the present invention relates to a process for preparing high yield sodium pyrithione from pyridine N-oxide. In particular, the present invention is directed to a process for making alkali metal pyrithione, which comprises reacting pyridine N-oxide with at least one sulfurination agent and at least one base agent. This reaction takes place in a solvent blend. The solvent blend is an organic solvent mixed with a surfactant. First, the alkali metal pyrithione, the sulfurination agent(s) and the base agent(s) are added to the solvent blend to form a first reaction mixture, where the sulfurination agent(s) and the base agent(s) are added in a predetermined molar ratio relative to the pyridine N-oxide. Next the first reaction mixture is heated to a first predetermined temperature where any water generated during the heating is removed. After heating, the reaction mixture is cooled to a second predetermined temperature. Once cooled, an aqueous solution is added to the cooled reaction mixture forming a two phase liquid having an organic layer and an aqueous layer. The aqueous layer is then separated from the two phase liquid before or after filtering. The two phase liquid or the aqueous layer is filtered to obtain a filter cake and a filtrate. The aqueous layer, after filtration is sparged with chemically inert gas into a trap, the trap containing an alkali metal hydroxide to form a second reaction mixture. Finally the alkali metal pyrithione is isolated from the second reaction mixture.

In another embodiment of the invention, the filter cake is then washed with an aqueous liquid and the aqueous liquid is captured after washing and is added to the filtrate prior to sparging.

In an aspect of the invention, the process yield of the alkali metal pyrithione is about 80% to 95%.

In an embodiment of the present invention, the surfactant is selected from a non-ionic surfactant or ionic surfactant or mixtures thereof. The amount of the surfactant added to the first organic solvent to form the solvent blend is from about 0.05 weight % to about 10 weight % based on the weight of the pyridine N-oxide.

In an additional embodiment of the present invention, the sulfurination agent is selected from elemental sulfur, sulfur chloride, and alkali metal polysulfides. When the sulfurination agent is elemental sulfur, the predetermined molar ratio of the elemental sulfur to the pyridine N-oxide may be from about 1 to about 3.

Various other embodiments of the present invention may also be used within the scope of the present invention. Some additional embodiment include, individually: a further step of adjusting the pH value of the separated aqueous layer to about 6.0-7.0; further comprising the step of adjusting the pH value of the second reaction mixture to about 7.0-10.0; the base agent is selected from hydrated sodium sulfide, sodium hydrosulfide, calcium hydroxide and alkali metal hydroxide; the first organic solvent is selected from diethylbenzene, dipropylbenzene, tetrahydronathelene, decahydronaphthalene, xylene, toluene and an alkylether such as ethylene glycol dialkyl ether such as ethylene glycol dimethyl or dibutyl ether, ethylene glycol diethyl ether, or organic amines; and/or the first predetermined temperature is from about 60° C. to about 210° C.

In an additional embodiment of the present invention, the heating may be accelerated to the first predetermined temperature by using microwaves.

In further embodiments of the present invention, the base agent may be an alkali metal hydroxide and wherein the predetermined molar ratio of the alkali metal hydroxide to the pyridine N-oxide may be from about 0.2 to about 3.5. In a further embodiment, the base agent is calcium hydroxide and wherein the predetermined molar ratio of the calcium hydroxide to the pyridine N-oxide may be from about 0.2 to about 1.5.

In further embodiments of the present invention, the base agent may a mixture of sodium sulfide and calcium hydroxide. The predetermined molar ratio of the sodium sulfide to the pyridine N-oxide is from about 0.4 to about 2.0 and the predetermined molar ratio of the calcium hydroxide to the pyridine N-oxide is from about 0.2 to about 1.5.

Another aspect of the present invention is a process of preparing polyvalent metal pyrithione forming an alkali metal pyrithione described above followed by reacting the alkali metal pyrithione with polyvalent metal salt to form polyvalent metal pyrithione. The counter ion for the polyvalent metal in the polyvalent metal salt may be a chloride, a sulfate, a nitrate, or an oxide. The polyvalent metal is a metal ion selected from Mg, Ca, Sr, Ba, Cu, Ag, Zr or Zn. The resulting polyvalent metal salts of pyrithione prepared in accordance with the process of the invention is a high purity polyvalent metal salts of pyrithione with white or off-white color zinc pyrithione.

These and other embodiments of the present invention, as well as its advantages and features, are described in more detail in conjunction with the text below.

DETAIL DESCRIPTION OF THE INVENTION

The present invention relates to a method of preparing polyvalent metal salts of pyrithione from pyridine N-oxide. The metal salts of pyrithione are formed at yields of about 80% and with purity acceptable for commercial applications. It has now been surprisingly found that a reaction of pyridine N-oxide 6 with sulfurination agent and a base agent in the presence of a suitable surfactant or dispersant agent and an organic solvent, in a specific molar or weight ratio at an elevated temperature, results in the formation of alkali metal pyrithione 4 having a yield of at least 80% (Scheme 3). Generally, the yield will be in the 80% to 95% range.

Scheme 3

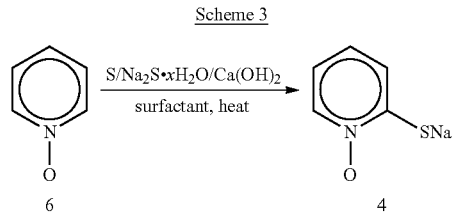

An embodiment of the present invention relates to the process for preparing alkali metal pyrithione, and includes reacting pyridine N-oxide, sulfurination agent(s) and a base agent(s) in an organic solvent at a predetermined temperature. The reactants N-oxide, sulfurination agent(s) and the base agents are present in the organic solvent in a predetermined molar ratio. Once the reaction is complete, the product mixture is cooled and mixed with water forming a two phase liquid having an aqueous layer and an organic layer. The aqueous layer s separated from the organic layer. The separated aqueous layer is filtered and the filter cake is optionally washed with excess water. The filtrate of the filtered aqueous layer. The aqueous layer is separated from the organic layer in the filtrate, and the separated filtrate is transferred to a neutralizer where the pH of the aqueous layer is adjusted to a desired value. In one embodiment of the present invention, the pH value is adjusted to about 6.0-7.0. The neutralized aqueous solution is sparged with a chemically inert gas into an alkali metal hydroxide trap. The pH of the resulting solution from the alkali metal hydroxide trap is adjusted to a basic condition with an alkali metal hydroxide solution. In one embodiment of the present invention, the pH value of the alkali metal hydroxide solution from the trap is adjusted to about 7.0-10.0. The resulting product solution is filtered to isolate aqueous alkali metal pyrithione.

Exemplary sulfurination agents that can be used in a process in accordance with the present invention include elemental sulfur, sulfur chloride, alkali metal polysulfides, and the like. In one embodiment of the present invention, a combination of elemental sulfur and sodium sulfide can be used as a sulfurination agent. It is noted that sodium sulfide may also act as a base agent. In another embodiment of the present invention, a combination of elemental sulfur and polysulfide can be used as a sulfurination agent, where polysulfide may be generated in situ from reaction between elemental sulfur and sodium sulfide or sodium hydroxide.

In one embodiment of the present invention, molar ratio of elemental sulfur to pyridine N-oxide 6 is from about 1.0 to about 3, the molar ratio of sodium sulfide to pyridine N-oxide 6 is from about 0.3 to about 1.0, and the molar ratio of calcium hydroxide to pyridine N-oxide 6 is from about 0.2 to about 1.5. In another embodiment of the present invention, the molar ratio of elemental sulfur to pyridine N-oxide 6 is from about 0.5 to 2.0, the molar ratio of sodium sulfide to pyridine N-oxide 6 is from about 0.2 to about 1.5, and the molar ratio of calcium hydroxide to pyridine N-oxide 6 is from about 0.2 to about 1.5. In one example of the present invention, the molar ratio of elemental sulfur to pyridine N-oxide 6 is from about 0.2 to 1.5. In general, about 60-63% hydrated sodium sulfide is used in a process in accordance with an embodiment of the present invention.

It has also been surprisingly found that a reaction of pyridine N-oxide 6 with alkali metal hydroxide, elemental sulfur, calcium hydroxide and a surfactant in an organic solvent, in a specific molar or weight ratio at an elevated temperature, results in the formation of alkali metal pyrithione 4. In one embodiment of the present invention, using sodium hydroxide as the alkali metal hydroxide results in the formation of sodium pyrithione having a yield of about 70%. In one embodiment of the present invention, the molar ratio of alkali metal hydroxide to pyridine N-oxide 6 is from about 1.5 to about 3.5, the molar ratio of elemental sulfur to pyridine N-oxide 6 is from about 1.5 to about 4, and the molar ratio of calcium hydroxide or calcium oxide to pyridine N-oxide 6 is from about 0.5 to about 1.5. In another embodiment of the present invention, the molar ratio of alkali metal hydroxide to pyridine N-oxide 6 is from about 1.0 to about 2.5, the molar ratio of elemental sulfur to pyridine N-oxide 6 is from about 1.5 to about 3.5, and the molar ratio of calcium hydroxide or calcium oxide to pyridine N-oxide 6 is from about 0.7 to about 1.0.

Exemplary alkali metal hydroxides that can be used in a process in accordance with an embodiment of the present invention include sodium hydroxide, lithium hydroxide and potassium hydroxide, or an alkali metal hydroxide generated in situ. Sodium hydroxide and sodium sulfide in the present invention can be other alkali metal hydroxide and sulfide such as lithium and potassium hydroxide and sulfide. However, when lithium, potassium hydroxide or sulfide is used, lithium or potassium pyrithione will be produced, respectively. In one embodiment of the present invention, sodium hydroxide, sodium sulfide and hydrated sodium sulfide are used in a powdered form. In another embodiment of the present invention, sodium hydroxide, sodium sulfide and hydrated sodium sulfide are used as an aqueous solution.

Calcium hydroxide is used as a co-base along with sodium sulfide to deprotonate pyridine N-oxide to form 2-carbon anion of the pyridine N-oxide. In one embodiment of the present invention, calcium oxide can be used in place of calcium hydroxide. Calcium hydroxide is generated in-situ from a reaction of calcium oxide with water present in the reaction mixture.

In one aspect of the present invention, a surfactant or dispersant is used to improve mixing, and prevent the reactants, reactive intermediates and products from sticking to the surface of the reactor, and thereby, improving the yield of sodium pyrithione 4. Exemplary surfactants or dispersants that can be used in the present invention include nonionic and ionic surfactants, such as DowFax® 2A1, DowFax® 4390, DowFax® 8390, C6L, C10L, BYKP-104, BYK P-105, Ideal CO-210, Plutonic 31R1, Plutonic 31R1, Witconol® NP-40, alkanat, EMPICOL® LX series, SURFONIC® POA series, and the like.

The amount of surfactant or dispersant that can be used in a process in accordance with an embodiment of the present invention is dependent on the type of surfactant or dispersant, and the concentration of pyridine N-oxide 6 in the reaction mixture. Generally, about 0.05% to about 10% by weight of the surfactant, based on the weight of the pyridine N-oxide, is used to improve mixing of the reaction mixture. Generally, the surfactant will be added in an amount of about 0.1 to about 2.0%, based on the weight of the pyridine N-oxide.

The pyridine N-oxide, sodium sulfide, surfactant or dispersant used in the present invention contain either free water or hydrated water. In one embodiment of the present invention, the content of water in pyridine N-oxide 6 is from about 1% to 50%, and in hydrated sodium sulfide is from about 30 to about 70%. In another embodiment of the present invention, the content of water in pyridine N-oxide 6 is from about 2% to about 10%, and in hydrated sodium sulfide is from about 40% to about 45%. The content of water in a commercial surfactant or dispersant is about 0% to about 70%. In some aspects of the present invention, all waters present in the pyridine N-oxide 6, the surfactant or dispersant, sodium sulfide and other reactants, and generated from the reactions are removed, during reactions, using a Dean-Stark trap device in order for the reactions to go to completion.

Solvent(s) or mixture of solvents suitable for use in a process in accordance with an embodiment of the present invention have a boiling point of at least 75° C. Exemplary solvents that can be use in the present invention include alkylbenzene such as diethylbenzene (DEB), dipropylbenzene (DIB), decahydronaphthalene, toluene and xylene. A co-solvent can be selected from glycol alkyl ethers such as diethylene glycol dimethyl ether, diethylene glycol dibutyl ether, dimethylsulfoxide (DMSO), amines and the like. These solvents can also be used as diluents for the reactants in reactions under controlled conditions. The quantity of solvent used for the reaction ranges from 5 to 20 times the weight, typically 7 to 12 times the weight, of pyridine N-oxide.

A reaction, in accordance with an embodiment of the present invention, is generally carried out at 60° C. to 210° C., at 180° C. to 200° C., or at 190° C. to 200° C., depending on the boiling point of solvent or diluents. The reaction time is typically dependent on reaction temperature and concentrations of the reactants. For example, the reaction generally takes about one hour to about seven hours at about 190° C., and about three to about four hours at about 200° C. to achieve about 95% conversion of pyridine N-oxide 6.

In some embodiments of the present invention, microwaves can be used to accelerate heating for producing sodium pyrithione 4 from a reaction mixture comprising pyridine N-oxide 6, sodium sulfide or sodium hydroxide, elemental sulfur, calcium hydroxide, and a surfactant in an organic solvent. Although yields of sodium pyrithione 4 from reactions using microwave heating are very similar to those with conventional heating, use of microwave accelerates heating and significantly improves efficiency of production of sodium pyrithione 4.

Another embodiment of the present invention relates to the process for preparing polyvalent metal pyrithione, and includes reacting pyridine N-oxide, sulfurination agent(s) and a base agent in an organic solvent at a predetermined temperature. The reactants N-oxide, sulfurination agent(s) and the base agent(s) are present in the organic solvent in a predetermined molar ratio. Once the reaction is complete, the product mixture is cooled and mixed with water, forming a two phase liquid having an organic layer and an aqueous layer. The aqueous layer is separated from the organic layer and then the aqueous layer is filtered. The filtering results in a filter cake and filtrate. The resulting filter cake is washed with excess aqueous solution, generally water. Alternately, the aqueous layer is separated from the organic layer in the filtrate after filtration. In any event, the separated aqueous layer is transferred to a neutralizer where the pH of the aqueous layer is adjusted to a desired value. In one embodiment of the present invention, the pH value is adjusted to about 6.0-7.0. The neutralized aqueous solution is sparged with a chemically inert gas into an alkali metal hydroxide trap. The pH of the resulting solution from the alkali metal hydroxide trap is adjusted to a basic condition with alkali metal hydroxide solution. In one embodiment of the present invention, the pH value of the alkali metal hydroxide solution is adjusted to about 7-10. The resulting solution is filtered to isolate aqueous alkali metal pyrithione. In the next step, polysulfide residues are removed from the aqueous alkali metal pyrithione solution, and then reacted with a polyvalent metal salt to form polyvalent metal pyrithione.

The is a process of preparing polyvalent metal pyrithione forming an alkali metal pyrithione described above followed by reacting the alkali metal pyrithione with polyvalent metal salt to form polyvalent metal pyrithione. Suitable polyvalent metal salts include, but are not limited to, salts from having a metal ion selected from Mg, Ca, Sr, Ba, Cu, Ag, Zr or Zn and a counter ion for the polyvalent metal in the polyvalent metal salt may be a chloride, a sulfate, a nitrate, or an oxide. The resulting polyvalent metal salts of pyrithione prepared in accordance with the process of the invention is a high purity polyvalent metal salts of pyrithione with white or off-white color zinc pyrithione.

The following examples of the present invention are further intended to describe and demonstrate, but in no way limited, the scope of the present invention. The examples are given solely for the purpose of illustration, and are not to be understood as limitations of the present invention since many variations therefore are possible within the scope.

In the following examples, HPLC and GC were used to analyze pyridine, pyridine N-oxide, sodium pyridine. Zinc and copper pyridine were analyzed using standard known methods, and zinc pyrithione color was measured using Gretag Macbeth Color-Eye®3100.

Example 1

A 1 L reactor was purged with nitrogen and charged with the following in the listed order and while stirring: 300 ml 1,3-diisopropylbenzene (DIB), 3.6 g DowFax*2A1 surfactant, 24.2 g (0.242 miles) 95% pyridine N-oxide, 11.0 g (0.343 miles) elemental sulfur, 22.2 g ground 60-63% $Na_2S$, and 17.6 g (0.242 miles) of $Ca(OH)_2$. The reaction mixture was heated and stirred to 200° C. for 3.5 hrs. About 14 ml $H_2O$ and 27 ml of DIB were collected from the Dean-Stark trap.

The reaction mixture was cooled to 70° C. and 200 ml of water was added. The mixture was filtered, and the filtered wet cake was washed with 3×45 ml water. The aqueous layer was separated and transferred to the neutralizer which was adjusted to pH 6.0-6.3 with 23.5 g 37% HCl and sparged with nitrogen for 1 hr into a 40% NaOH trap. The pH of the reaction solution was then adjusted to ~8.0 with 50% NaOH. The resulting mixture was filtered to give 353.3 g of aqueous sodium pyrithione solution. HPLC analysis showed that the solution contained 8.07% sodium pyrithione. The yield was 79.7% with 93.7% pyridine N-oxide conversion.

Example 2

With the same set up described in Example 1, the mixture of 300 ml 1,3-isopropylbenzene and 36.65 g 55.39% pyridine N-oxide solution (20.30 g 100% pyridine N-oxide) was stirred at 170° C. for 1.5 hrs. 16 ml $H_2O$ and 6 ml of DIB were recovered from the trap. The reactor was cooled to 85° C. and 3.13 g DowFax*2A1, 15.60 g $Ca(OH)_2$, 20.53 g ground 60% $Na_2S$ and 10.23 g sulfur were added in the order.

The reaction mixture was heated to 202° C. with stirring for 2 hrs. 16 ml water was found in the trap. The reactor was cooled to 90° C. and 170 ml of water was added. The reaction mixture was filtered at 25° C., and the solid was washed with ~250 ml water. The aqueous layer was separated and transferred to a 1 L 3-neck flask, and was adjusted to pH 6.0 with 37% HCl at stirring and sparged with nitrogen for 1 hr, and was then adjusted to ~8.0 with 50% NaOH. The resulting mixture was filtered to give 489 g of sodium pyrithione solution. HPLC analysis showed that yield of sodium pyrithione was 73.6% with 93.6% pyridine N-oxide conversion.

Example 3

The experiment was carried out in a manner as described in example 1, but was run at 190° C. for 6.5 hrs. 83.8% yield was obtained with 94.1% conversion of pyridine N-oxide.

Example 4

The experiment was carried out in a manner as described in example 1, but was run at 183° C. for 4 hours using pyridine N-oxide, elemental sulfur, sodium hydroxide and calcium oxide in a molar ratio of 1.0:3.5:2.5:1.0 in diethylbenzene. 68% yield of sodium pyrithione was obtained with 88% conversion of pyridine N-oxide.

Example 5

The experiment was carried in a manner as described in example 1, but microwave was used to heat the reaction mixture for 1.5 hrs at 200° C. The reaction gave 74.1% yield of sodium pyrithione with 90.9% conversion.

Example 6

The experiment was carried out in a manner as described in example 5, but a Teflon reactor was used. With microwave heating at 200° C. for 1.5 hrs, the reaction gave 80.8% yield of sodium pyrithione with 91.4% conversion.

While the invention has been described above with references to specific embodiments thereof, it is apparent that many changes, modifications and variations can be made without departing from the inventive concept disclosed herein. Accordingly, it is intended to embrace all such changes, modifications and variations that fall within the spirit and broad scope of the appended claims. All patent applications, patents and other publications cited herein are incorporated by reference in their entirety.

What is claimed is:

1. A process for preparing an alkali metal pyrithione comprising the steps of:
   adding pyridine N-oxide, at least one sulfurination agent and at least one base agent to a solvent blend, the solvent blend containing a surfactant and a first organic solvent, to form a first reaction mixture; wherein the sulfurination agent and the base agent are added in a predetermined molar ratio relative to the pyridine N-oxide;

heating the first reaction mixture to a first predetermined temperature;

cooling the first reaction mixture to a second predetermined temperature;

adding an aqueous solution to the cooled reaction mixture to form a two phase liquid having an organic layer and an aqueous layer;

filtering the aqueous layer or the two phase liquid to obtain a filter cake and a filtrate;

separating the aqueous layer from the two phase liquid before or after filtering;

sparging the aqueous layer or the filtrate with a chemically inert gas into a trap, the trap comprising an alkali metal hydroxide to form a second reaction mixture; and isolating the alkali metal pyrithione from the second reaction mixture.

2. The process of claim 1, wherein water is generated during the heating of the first reaction mixture and water is continuously removed from the first reaction mixture during heating.

3. The process of claim 1, further comprising washing the filter cake with an aqueous liquid and capturing the aqueous liquid after the washing and combining the captured aqueous liquid with the filtrate.

4. The process of claim 1, wherein the sulfurination agent is selected from a group consisting of elemental sulfur, sulfur chloride, and alkali metal polysulfides.

5. The process of claim 1, wherein the surfactant is selected from a group consisting of a non-ionic surfactant and an ionic surfactant.

6. The process of claim 1, wherein the solvent blend contains the surfactant in an amount from about 0.05 weight % to about 10 weight % of the pyridine N-oxide.

7. The process of claim 1, further comprising the step of adjusting the pH value of the separated aqueous layer to about 6.0-7.0.

8. The process of claim 1, further comprising the step of adjusting the pH value of the second reaction mixture to about 7.0-10.0.

9. The process of claim 1, wherein the base agent is selected from a group consisting of hydrated sodium sulfide, sodium hydrosulfide, calcium hydroxide and alkali metal hydroxide.

10. The process of claim 1, wherein the first organic solvent is selected from a group consisting of diethylbenzene, dipropylbenzene, tetrahydronathelene, decahydronaphthalene, xylene, toluene and an alkylether such as ethylene glycol dialkyl ether such as ethylene glycol dimethyl or dibutyl ether, ethylene glycol diethyl ether, and organic amines.

11. The process of claim 1, wherein the first predetermined temperature is from about 60° C. to about 210° C.

12. The process of claim 1, further comprising the step of accelerating the heating of the first reaction mixture to the first predetermined temperature, wherein the heating is accelerated by microwaves.

13. The process of claim 1, wherein the sulfurination agent is elemental sulfur and wherein the predetermined molar ratio of the elemental sulfur to the pyridine N-oxide is from about 1 to about 3.

14. The process of claim 1, wherein the at least one base agent is calcium hydroxide and wherein the predetermined molar ratio of the calcium hydroxide to the pyridine N-oxide is from about 0.2 to about 1.5.

15. The process of claim 1, wherein the at least one base agent is sodium sulfide wherein the predetermined molar ratio of the sodium sulfide to the pyridine N-oxide is from about 0.2 to about 1.0.

16. The process of claim 1, wherein the solvent blend contains the surfactant in an amount from about 0.2 weight % to about 20 weight % of the pyridine N-oxide;

the at least one base agent is calcium hydroxide and wherein the predetermined molar ratio of the calcium hydroxide to the pyridine N-oxide is from about 0.2 to about 1.5 and sodium sulfide wherein the predetermined molar ratio of the sodium sulfide to the pyridine N-oxide is from about 0.2 to about 1.0;

the sulfurination agent is elemental sulfur and wherein the predetermined molar ratio of the elemental sulfur to the pyridine N-oxide is from about 1 to about 3;

the first organic solvent is selected from a group consisting of diethylbenzene, dipropylbenzene, tetrahydronathelene, decahydronaphthalene, xylene, toluene and an alkylether such as ethylene glycol dialkyl ether such as ethylene glycol dimethyl or dibutyl ether, ethylene glycol diethyl ether, and organic amines; and the process further comprises the step of adjusting the pH value of the separated aqueous layer to about 6.0-7.0 and the step of adjusting the pH value of the second reaction mixture to about 7.0-10.0.

17. A process for preparing a polyvalent metal pyrithione comprising:

forming an alkali metal pyrithione comprising an alkali metal according to the process of claim 1 and reacting the alkali metal pyrithione with a polyvalent metal salt comprising a polyvalent metal to form the polyvalent metal pyrithione.

18. The process of claim 17, wherein the counter ion for the polyvalent metal in the polyvalent metal salt is selected from a group consisting of chloride, sulfate, nitrate, and oxide.

19. The process of claim 17, wherein the alkali metal is selected from a group consisting of lithium, sodium and potassium.

20. The process of claim 17, wherein the polyvalent metal is selected from a group consisting of Mg, Ca, Sr, Ba, Cu, Ag, Zr and Zn.

21. A process for preparing a polyvalent metal pyrithione comprising:

forming an alkali metal pyrithione according to the process of claim 16; and reacting the alkali metal pyrithione with a polyvalent metal salt to form the polyvalent metal pyrithione.

22. The process according to 21, wherein the polyvalent metal salt is selected from a group consisting of a chloride, a sulfate, a nitrate, and an oxide of Mg, Ca, Sr, Ba, Cu, Ag, Zr or Zn.

* * * * *